United States Patent [19]

Lee et al.

[11] Patent Number: 4,637,938

[45] Date of Patent: Jan. 20, 1987

[54] METHODS OF USING SELECTIVE OPTICAL EXCITATION IN DEPOSITION PROCESSES AND THE DETECTION OF NEW COMPOSITIONS

[75] Inventors: Henry Lee, Somerville; John P. deNeufville, Mendham, both of N.J.; Stanford R. Ovshinsky, Bloomfield Hills, Mich.

[73] Assignee: Energy Conversion Devices, Inc., Troy, Mich.

[21] Appl. No.: 524,923

[22] Filed: Aug. 19, 1983

[51] Int. Cl.[4] ......................... B05D 3/06; B05D 5/12
[52] U.S. Cl. .................................. 427/53.1; 136/258; 252/372; 427/86; 436/35; 436/172
[58] Field of Search ...................... 427/34, 53.1, 8, 86; 436/35, 172; 204/192 S, 192 P; 136/258; 430/128; 252/372

[56] References Cited

U.S. PATENT DOCUMENTS

| | | | |
|---|---|---|---|
| 4,007,009 | 2/1977 | Wright | 436/172 X |
| 4,217,374 | 8/1980 | Ovshinsky et al. | 427/53.1 X |
| 4,448,801 | 5/1984 | Fukuda et al. | 427/86 X |
| 4,472,492 | 9/1984 | Kanbe et al. | 430/128 X |

OTHER PUBLICATIONS

Bilenchi, Renzo et al., *Laser Induced Chemical Vapor Deposition of Hydrogenated Amorphous Silicon*, pp. 199-205, 1983.

Okamoto, K. et al., *Current-Assisted Laser Annealing of Polysilicon Films*, pp. 809-813, Appl. Phys. Lett. 42(9), 1 May 1983.

Meunier, M. et al., *Hydrogenated Amorphous Silicon Produced by Laser Induced Chemical Vapor Deposition of Silane*, Appl. Phys. Lett. 43(3) 1 Aug., 1983.

"Plasma Spectroscopy—Glow Discharge Deposition of Hydrogenated Amorphous Silicon", Akihisa Matsuda and Kazunobu Tanaka, *Thin Solid Films*, 92 (1982) 171-187.

"Detection of $CF_2$ Radicals in a Plasma Etching Reactor by Laser-Induced Fluorescence Spectroscopy", P. J. Hargis, Jr. and M. J. Kushner, *Appl. Phys. Lett.*, 40(9), 1 May 1982, pp. 779-781.

"Laser Diagnostics of Plasma Etching: Measurement of $Cl_2^+$ in a Chlorine Discharge", V. M. Donnelly, D. L. Flamm, and G. Collins, *J. Vac. Sci. Technol.*, 21(3), Sep./Oct. 1982.

"Pulsed UV Laser Raman Spectroscopy of Silane in a Linear-Flow Chemical Vapor Deposition Reactor", W. G. Breiland and M. J. Kushner, *Appl. Phys. Lett.*, 42(4), 15 Feb. 1983. pp. 395-397.

"Measurement of Spatially Resolved Gas-Phase Plasma Temperatures by Optical Emission and Laser-Induced Fluorescence Spectroscopy", Glenn P. Davis and Richard A. Gottscho, *J. Appl. Phys.*, 54(6), Jun. 1983, pp. 3080-3086.

"Observation of HSiCl in a Chemical Vapor Deposition Reactor by Laser-Excited Fluorescence", Pauline Ho and William G. Breiland, *Appl. Phys. Lett.*, 43(1), Jul. 1, 1983, pp. 125-126.

*Primary Examiner*—Michael R. Lusignan
*Attorney, Agent, or Firm*—Marvin S. Siskind; Ronald W. Citkowski

[57] ABSTRACT

The present invention generally relates to the use of fluorescence signals obtained by selective optical excitation to detect and monitor a species present during a flow reaction or decomposition of various reactants. These reactions were analyzed in situ using a tunable laser as a selective excitation source in combination with a reactor inducing such reactions with a diffusion flame or a plasma. The resultant spectra and analysis presented herein demonstrates the detection of new compositions like SiHF in the gas phase. The invention allows for pinpoint spatial probing of the reactor without perturbing the reaction. Thus, a deposition process can be controlled by monitoring a selected species and adjusting the deposition reaction parameters in response to the species' mere detection or relative concentration. The invention also contemplates perturbing deposition reactions by selectively exciting a species present in the deposition reaction to modify the deposited material so that the quality of the deposited material improves. Specifically, improved photovoltaic devices which include photoconductive material made in accordance with the present invention are disclosed herein.

24 Claims, 9 Drawing Figures

METHODS OF USING SELECTIVE OPTICAL EXCITATION IN DEPOSITION PROCESSES AND THE DETECTION OF NEW COMPOSITIONS

BACKGROUND OF THE INVENTION

This invention relates generally to the use of optical excitation, particularly induced by a tunable laser, for the detection of new compositions and improved methods of depositing a material like a photoconductive film on a substrate.

Various deposition processes like glow-discharge and chemical vapor deposition have been used for producing films and coatings for application in many areas, e.g. photovoltaics, microelectronics, electroptics, and superconductors. Despite the development of these processes as a sophisticated technological art, the fundamental physical and chemical processes involved are still not fully understood.

The lack of detailed information is understandable because the deposition environment is quite difficult to study analytically. Over the years a number of in situ analytical techniques have been applied to the deposition environment. These techniques, however, have a number of limitations which prevents a detailed understanding of the deposition process. For example, mass spectroscopy and vapor chromatography both require physical probes and/or remote sensing apparatus and therefore may not record the true distribution of chemical species inside a deposition reactor. Mass spectroscopy also relies upon known fragmentation patterns of calibrated molecules. Often these patterns overlap and therefore obscure the patterns of intermediate or transient products of the reaction taking place in the deposition reactor.

Other examples of analytical techniques are optical absorption and emission spectroscopy. Optical absorption spectroscopy lacks spacial resolution in three dimensions and is much less sensitive than laser-induced fluorescence, precluding its use for the detection of species present in low concentrations or in the vicinity of the important gas-surface interface region. Emission spectroscopy by its very nature can only detect species that are in vibrationally or electronically excited states. The concentrations of species in the ground state far exceed those in the excited state and thus the method becomes effective only in monitoring a small fraction of the transient species present in the deposition process. Also, the excitation rate from the ground state to the observed excited state is often unknown and may depend on external parameters such as gas pressure and flow rate. Another limitation of these analytical techniques is that they do not provide a non-perturbing pinpoint probe that can accurately measure low, i.e. sub-Torr, concentrations of highly reactive chemical species in the presence of rapidly changing chemical and temperature fields.

There have been particular problems in measuring the energy distributions of particles in glow discharges, thus complicating the monitoring of the plasma used in photovoltaic film manufacturing. Reaction rates, available product channels, and transport phenomena all depend upon the partitioning of energy in the discharge. Because of the nonequilibrium nature of glow discharges, however, the distribution of energy among different species and among different degrees of freedom cannot be characterized simply by one temperature. The extent to which different temperatures are needed for each degree of freedom and for each species is not known completely. Also, not every discharge system used in photovoltaic processing provides a convenient, optically emitting species from which a temperature measurement can be made.

A variety of transient atomic and molecular species are produced in chemical vapor deposition, diffusion flame, and glow-discharge reactors by pyrolysis, chemical reactions, or electron bombardment. Some of these species may play a prominent role in the deposition of the film itself. Monitoring their concentrations accurately and with a nondestructive analytical technique would be very helpful in understanding the fabrication of the films. It is even more difficult to monitor the existence of transient species which may affect the quality of the film or coating being deposited if the species itself is not optically emitting or its emissions are not resolvable by the techniques described above.

In particular, photovoltaic quality films of amorphous $SiH_xF_y$ prepared by the plasma-induced reaction of, for example, $SiF_4$ and $H_2$, appear to contain unusual bonding configurations involving the intimate association of silicon with both fluorine and hydrogen atoms. The creation of radical sub-fluorides of silicon has been suggested as a mechanism for the deposition of such films. The presence of various excited-state neutral silicon radical species, i.e. SiF, SiH, $SiF_3$, and Si has been demonstrated through the use of optical emission techniques in diffusion flames. Other radicals, especially in the ground state, have escaped detection and thus have hindered analysis of the effect these radical species have on the quality of the deposited film.

SUMMARY OF THE INVENTION

The limitations discussed above are overcome by the use of selective optical excitation. First, optically excited fluorescence emission induced, for example, by a high or low power laser is an analytical technique which directly measures the ground-state concentration of a particular species. Analysis of a reaction is advantageously used as a non-perturbative probe capable of pinpoint spatial accuracy. Second, selective optical excitation induced, for example, by a relatively high power laser can be an advantageous modification technique for improving the quality of deposited film. A relatively high power laser can be used as a perturbative means for exciting a selected species to modify the deposition reaction. Thus, the depositing process can be accurately monitored and controlled to produce the desired film deposit.

Figure 2:
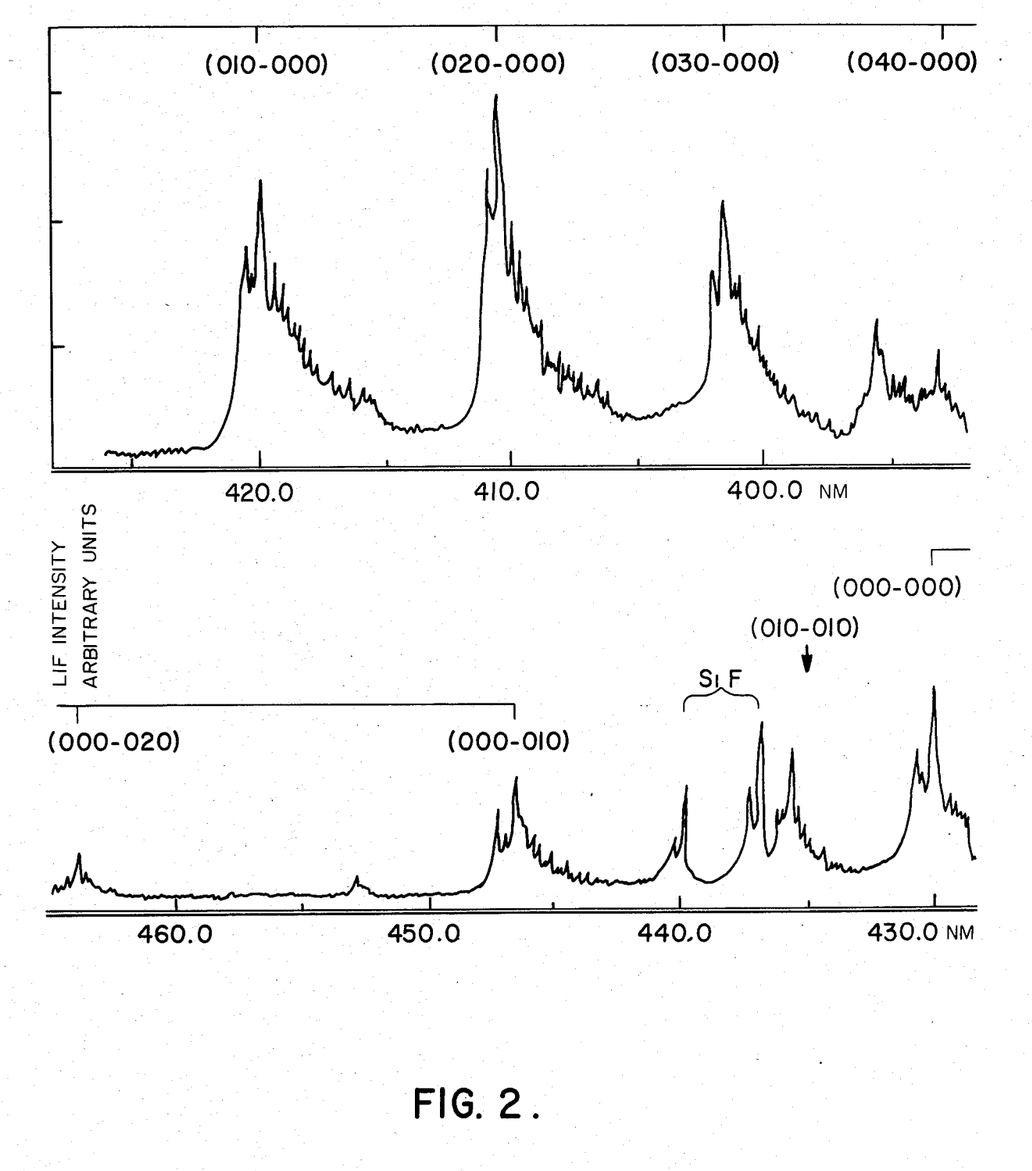
FIG. 2 is a spectrum of laser-induced fluorescence excitation obtained from the flow reaction of $SiH_4$ and $F_2$ in a diffusion flame reactor demonstrating the detection of HSiF and SiF with assignments made on the most intense peak of each band head.
Figure 4:
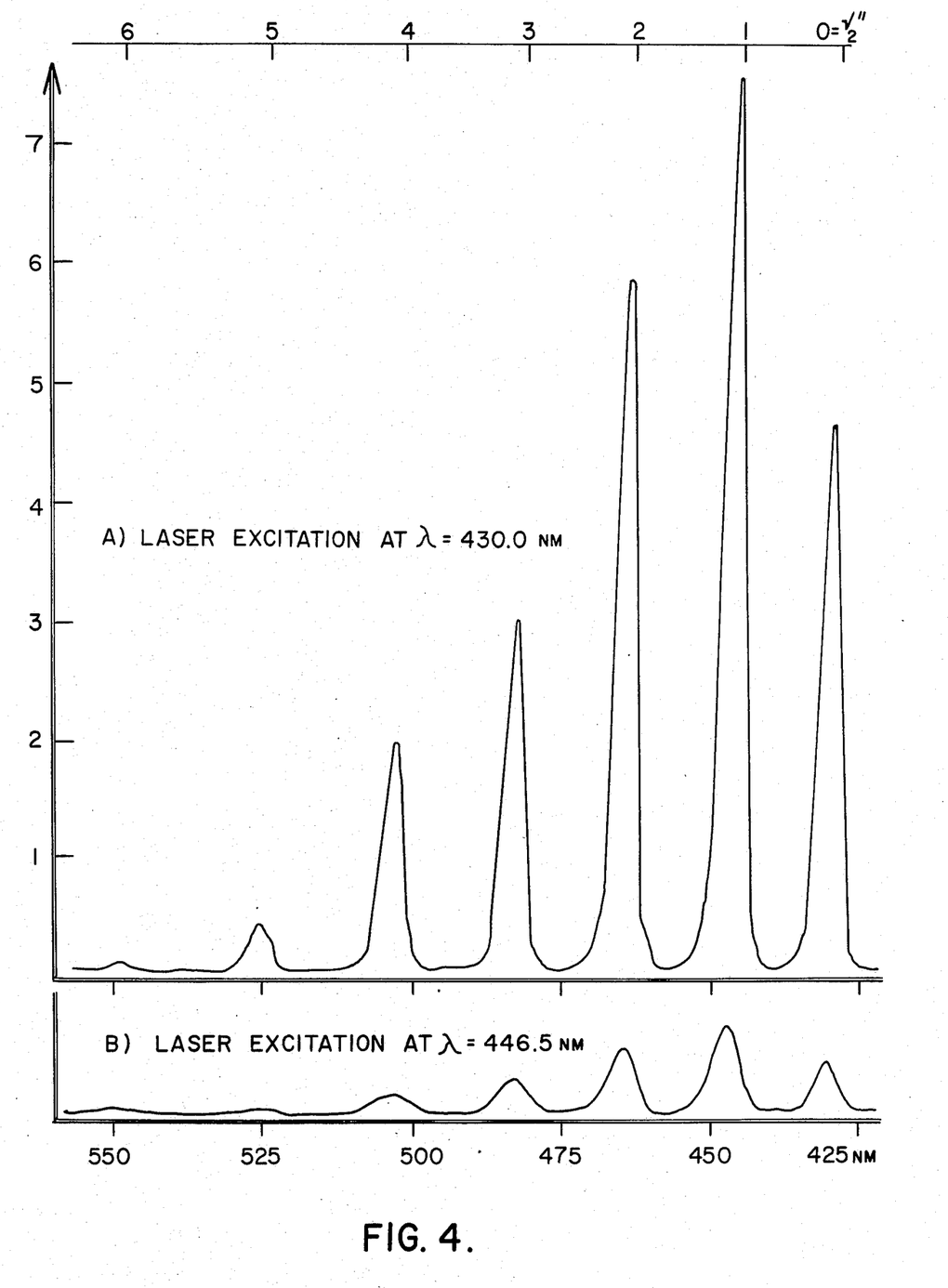
FIG. 4 is a spectrum of resolved laser-induced fluorescence emission demonstrating the detection of SiHF.

The present invention includes a gaseous composition having the formula SiHF. Also included is a composition containing the elements silicon, hydrogen, and fluorine which exhibits characteristic fluorescence emission at the following wavelengths expressed in nanometers: 430.0, 446.5, 464.5, 483.5, 503.5, and 548.9, as illustrated in FIG. 4. The composition also exhibits characteristic excitation at the following wavelengths expressed in nanometers: 430.0, 420.0, 410.5, 401.5, and 393.0, as illustrated in FIG. 2.

The present invention also includes methods of detecting a species in a flow reaction occuring in either a plasma or a diffusion flame which includes the step of inducing the fluorescence of said species with a laser.

Another method contemplated by the invention is for depositing a material on a substrate including the steps of inducing a deposition reaction having at least one reactant. The deposition reaction is in operative contact with a substrate so that the product of the deposition reaction is a body of material deposited on the substrate. The method further includes detecting a species in the deposition reaction and measuring the relative concentration of the species. Another step deposits the material on the substrate.

Another contemplated method deposits a photoconductive film by inducing a deposition reaction having at least one reactant. The deposition reaction is in operative contact with the substrate so that the product of the deposition reaction is a photoconductive film deposited on the substrate. The method further includes detecting a transient species having a stable excited state by inducing the fluorescence of the species with an optical excitation source and measuring the relative concentration of the species. Another step deposits the photoconductive film on the substrate.

A novel method of depositing an improved photoconductive film includes the step of inducing a deposition reaction in operative contact with a substrate so that the product of the deposition reaction is a photoconductive film deposited on the substrate. The deposition reaction is modified by exciting an effective concentration of a species so that the deposited photoconductive film is modified. The species is a precursor to the deposited film. Another step deposits the photoconductive film on the substrate.

The present invention also includes an apparatus for depositing material which includes a reactor for inducing a deposition reaction having at least one reactant. An optical excitation source is positioned for probing the reactor and a substrate is positioned in operative contact with the deposition reaction in the reactor. The apparatus includes means for detecting a species in the deposition reaction, inducing the fluorescence of the species with the optical excitation source, and measuring the relative concentration of the species.

Another apparatus embodiment contemplated by the invention includes a reactor for inducing a deposition reaction. The deposition reaction includes a species which is a precursor to the material deposited as the product of the deposition reaction. A substrate is positioned in operative contact with the deposition reaction in the reactor. The apparatus includes means for exciting an effective concentration of the species to a stable excited state in order to perturb the deposition reaction by operative contact therewith and modify the deposited material.

The invention also includes an improved photoconductive material and an improved photovoltaic device made from such a material. The photoconductive material is deposited while in operative contact with an effective concentration of a species for modifying said material. The species is a precursor to a material deposited as the product of a deposition reaction and is induced to a stable excited state during the deposition of the material.

DETAILED DESCRIPTION OF THE DRAWINGS

DETAILED DESCRIPTION OF THE INVENTION

The present invention generally relates to the use of fluorescence signals obtained by selective optical excitation to detect and monitor a species present during a flow reaction or decomposition of various reactants. These reactions were analyzed in situ using a tunable laser as a selective excitation source in combination with a reactor inducing such reactions with a diffusion flame or plasma. The resultant spectra and analysis presented below demonstrates the detection of a species like SiHF in the gas phase. The invention allows for pinpoint spatial probing of the reactor without perturbing the reaction. Thus, a deposition process can be controlled by monitoring a selected species and adjusting the deposition reaction parameters in response to the species' mere detection or relative concentration. The invention also contemplates perturbing deposition reactions by selectively exciting a species present in the deposition reaction to modify the deposited material so that the quality of the deposited material improves.

A fluorescent species can be excited by electromagnetic radiation and, as a consequence, reemit radiation either of the same wavelength or of a modified wavelength. At least one of the excited states of a species should be attractive or stable, otherwise the species will dissociate upon excitation. An excited species can return to its ground state by any of several mechanistic paths; the favored route is the one that minimizes the lifetime of the excited state. Thus, if deactivation by fluorescence is rapid with respect to other processes such emission is observed. On the other hand, if a radiationless path has a more favorable rate constant, fluorescence is either absent or less intense. Fluorescence spectroscopy is most useful in analyzing systems incorporating structural and environmental features that cause the rate of radiationless relaxation or deactivation reactions to be slowed to a point where the emission reaction can compete kinetically.

Figure 1:
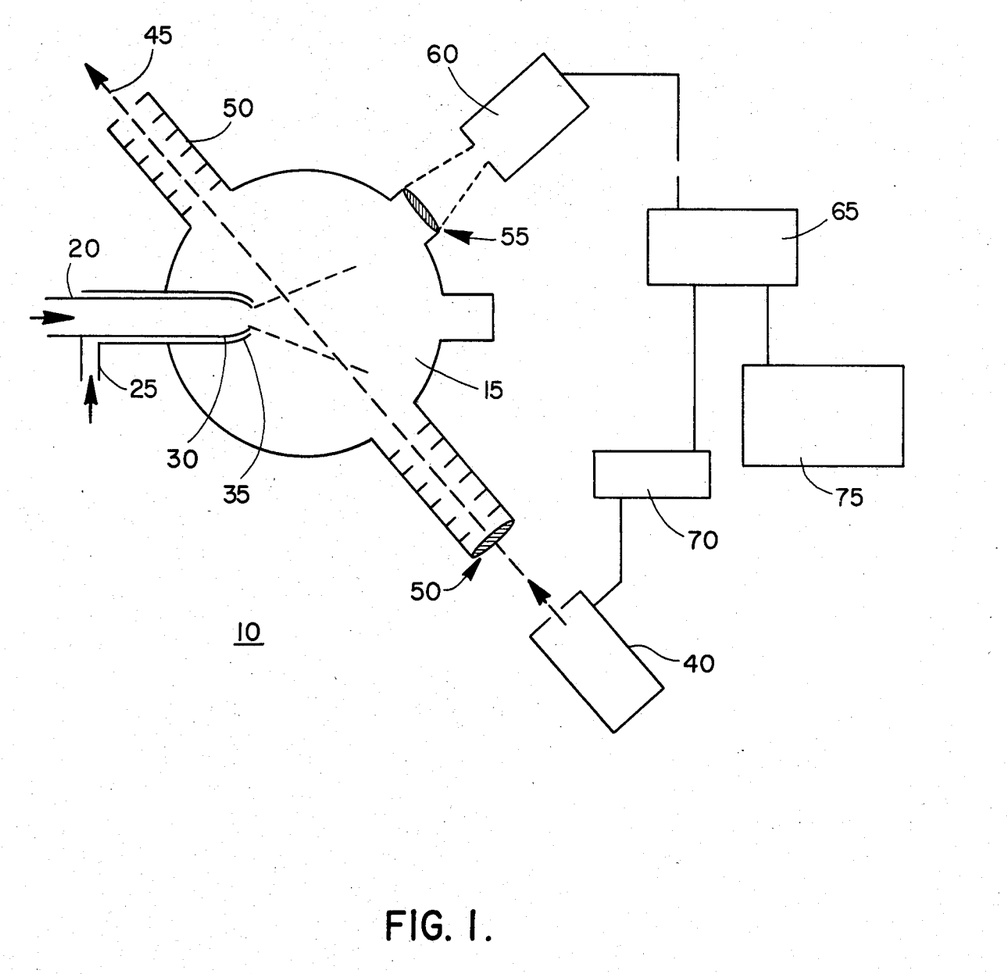
FIG. 1 is a schematic of an illustrative apparatus using the methods of the invention for probing a diffusion flame reactor by laser-induced fluorescence.

A schematic of a laser-induced fluorescence apparatus 10 contemplated by the present invention is illustrated in FIG. 1. The reactant gases are introduced into the reactor 15 through two concentric glass tubings 20, 25 with 3 mm diameter tapered ends 30, 35. The ground-state radicals produced in the reaction are excited by a PAR Dyescan 2100 pulsed tunable dye laser 40 which uses a pulse width of 5 ns. and a bandwidth 0.04 nm. in the region of 390–470 nm. The laser beam 45 enters the reactor 10 through a series of black baffles 50 designed to reduce scattered laser light. An excitation spectrum is obtained by focusing the fluorescence with an (f/4) lens system 55 onto a photomultiplier 60 with a EMI 9885A bialkali cathode (not shown), and the resulting signal is averaged by a PAR 165 boxcar 65. A trigger mechanism 70 connects the laser 40 to the boxcar 65. Time-resolved fluorescence decays are displayed on a recorder 75 with 2 ns. resolution by the boxcar 65. Other means for detecting a species in a deposition reaction, inducing fluorescence of the species and measuring the relative concentration of the species also are contemplated by the invention. Other selective optical excitation sources are suitable.

The species SiHF ($\tilde{X}\ ^1A'$) was produced in a flow reaction of silane with fluorine using a diffusion flame typically with a 4:1 mole ratio at a total pressure of 0.05–0.15 Torr and flow rates of 2–5 sccm. The fluorescence in much of the excitation region was sufficiently strong to allow a spectral resolution to be made. During these measurements, the laser 40 was first set at a predetermined frequency corresponding to a band head; the resulting fluorescence was then focused onto the entrance slit of a Plasmascan PSS-2M monochromator (not shown) having a resolution of 3.5 nm. usually scanned at 10-20 nm./min. The photomultiplier 60 attached to the exit slit senses the signal which is averaged by the boxcar 65 with a time constant of 100 $\mu$s.

FIG. 2 is a spectrum of fluorescence excitation obtained between 390 and 470 nm at laser power levels of 10–20 $\mu$J/pulse produced during the above-identified reaction. The spectrum has been normalized for laser intensity and detector spectral response. In contrast to the two narrow bands of SiF (A $^2\Sigma+ - X^2\pi$) located at 436.8 and 440.0 nm, both of which are shaded towards the infrared region, all the other intense bands are significantly broader and are shaded towards the ultraviolet region. This spectrum is remarkably similar in appearance to the chemiluminescence spectrum of SiHCl, reported in Conner et al., J. Amer. Chem. Soc. 99 (1977) 2541, except that the bands are shifted to the blue by approximately 2550 cm$^{-1}$. The identification and analysis of this SiHF band system was made by comparing it with previously reported spectra of SiHCl and SiHBr reported in Herzberg et al., Can. J. Phys. 42 (1964) 395; the SiHI spectrum reported in Billingsley et al., Can. J. Phys. 50 (1972) 531; and the GeHCl spectrum reported in Patel et al., Can. J. Phys. 55 (1977) 1518. Accordingly, we have assigned the five prominent peaks located at 430.0, 420.0, 410.5, 401.5, and 393.0 nm of FIG. 2 to the band heads of this transition, with $v'=0,1,2,3$ and 4, respectively. Following this assignment, the bending frequency $v_2'$ for the upper $^1A''$ state is found to be roughly 560 cm$^{-1}$.

Another flow reaction was performed under the above stated conditions between silane and XeF$_2$. A spectrum essentially identical to the one illustrated in FIG. 2 was obtained which again demonstrated the detection of SiHF. This also illustrates the use of other fluorine containing compounds as a reactant.

Figure 3:
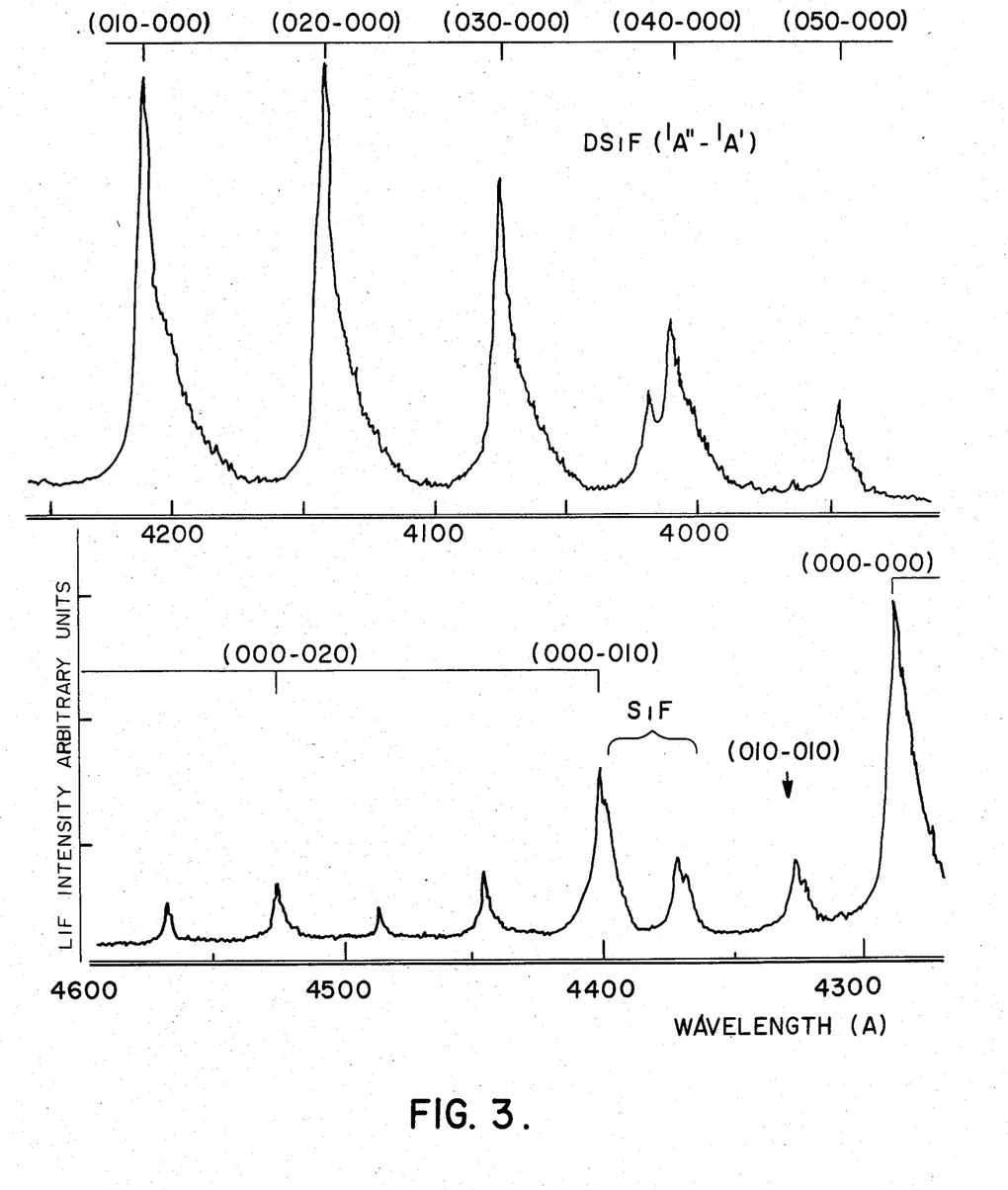
FIG. 3 is a spectrum of laser-induced fluorescence excitation obtained from the flow reaction of $SiD_4$ and $F_2$ in a diffusion flame reactor demonstrating the detection of DSiF.

To obtain a laser-induced excitation spectrum of SiDF, the reaction of SiD$_4$ and fluorine was run under the same conditions described above. The SiD$_4$ was obtained in 98.5% purity from Cambridge Isotope Laboratories. FIG. 3 presents the spectrum identifying the bands for SiDF which provided further confirmation of the band assignments for SiHF.

FIG. 4 is a spectrum of resolved fluorescence emission accompanying laser excitation at 430.0 and 446.5 nm. From the observed band spacings in these spectra, the bending frequency $v_2''$ of the SiHF in the ground state is found to be roughly 860 cm$^{-1}$, in excellent agreement with the value of 859 cm$^{-1}$ derived from a recent infra-red analysis of matrix-isolated SiHF, in Ismail et al., J. Chem. Phys. 77 (1982) 1626.

Figure 5:
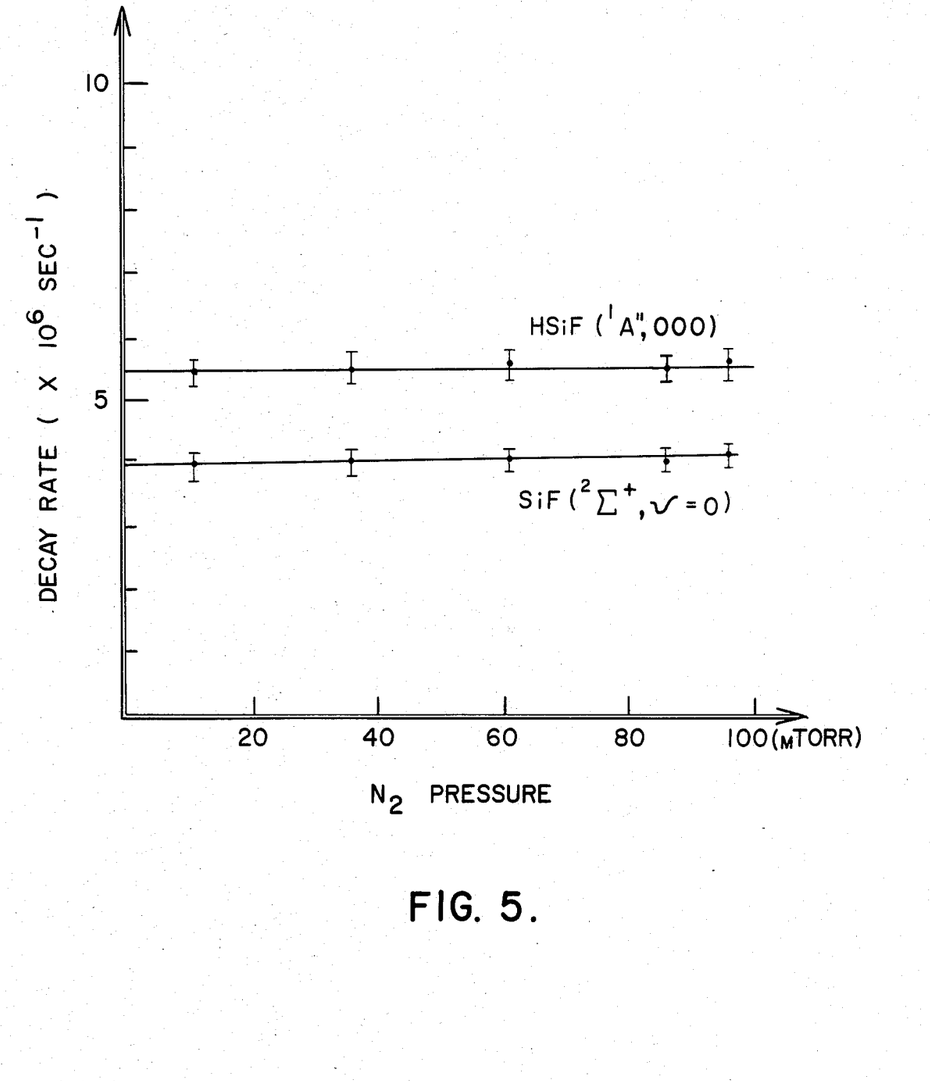
FIG. 5 illustrates the decay rates of SiHF and SiF in their lowest vibrational level as a function of $N_2$ pressure.

The decay rates of SiF (A $^2\Sigma+$) and SiHF ($\tilde{A}\ ^1A''$) in their lowest vibrational level were measured as a function of the pressure of N$_2$, which was introduced into the reaction chamber. The laser excitations were centered at 436.8 and 440.0 nm for SiF and at 430.0 nm. for SiHF. As shown in FIG. 5, these rates appeared to be fairly insensitive to N$_2$, pressure at least in the pressure range of 10–100 mTorr. Moreover, the rates were found to be invariant with excitation wavelength within a given vibronic band. When extrapolated to zero N$_2$ pressure, these rates are expected to yield reasonable values for the radiative lifetimes, $\tau_R$. From these measurements, $\tau_R$ for SiF and SiHF are found to be 255±10 ns. and 185±10 ns., respectively. We note that our $\tau_R$ value for SiF is 10–15% longer than that reported by Armstrong et al., J. Chem. Phys. 71 (1979) 2433, from their studies of this reaction. The discrepancy may be explained by the significantly higher pressure regimes (up to 10 Torr) under which Armstrong et al. performed their measurements.

Figure 6:
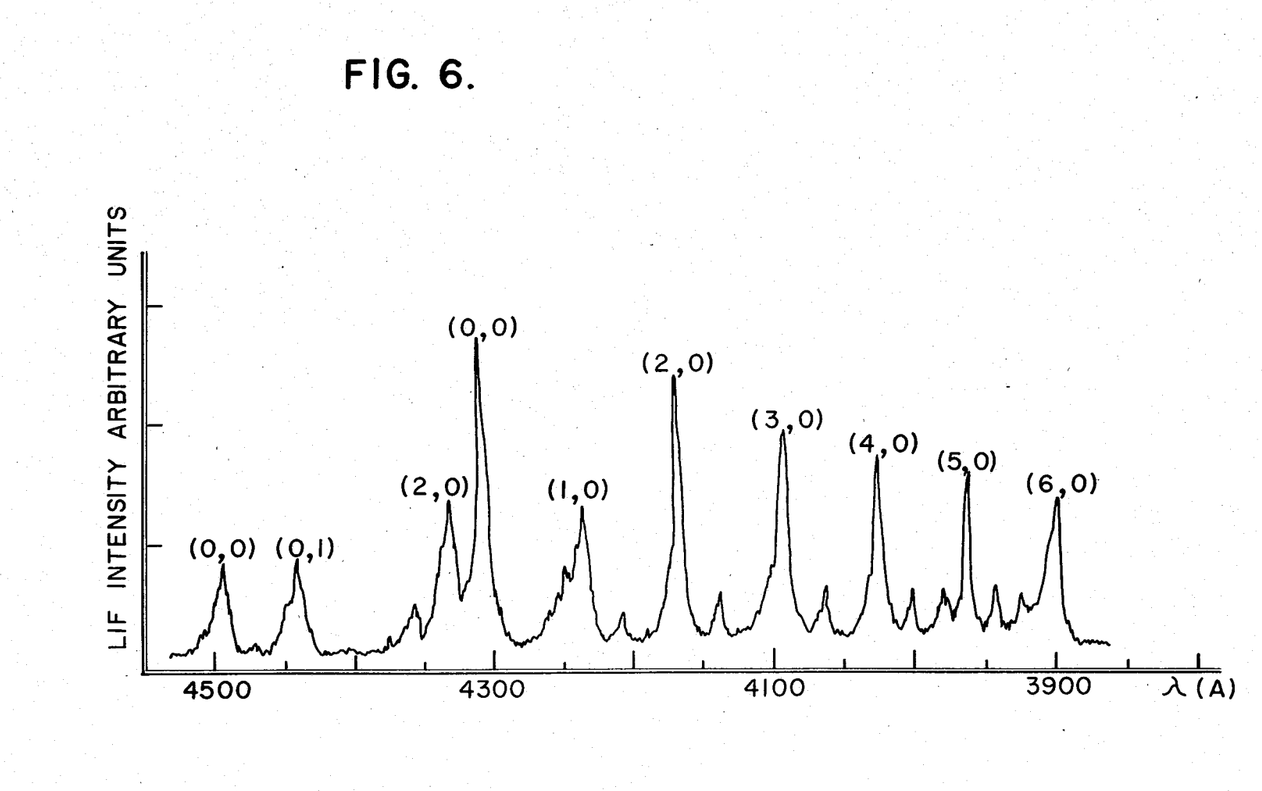
FIG. 6 is a spectrum of laser-induced fluorescence excitation obtained from the flow reaction of $GeH_4$ and $F_2$ in a diffusion flame reactor demonstrating the detection of GeF.

FIG. 6 is a spectrum of laser-induced fluorescence emission of the flow reaction of GeH$_4$ and fluorine run under the same conditions described above. The eight prominent peaks at 396.5, 402.8, 409.4, 416.3, 423.6, 431.1, 433.2, 443.7, and 449.2 nm. are assignable to GeF. The spectrum demonstrates the detection of transient species GeF and the usefulness of this invention for the detection of species other than those containing the silicon atom.

Figure 7:
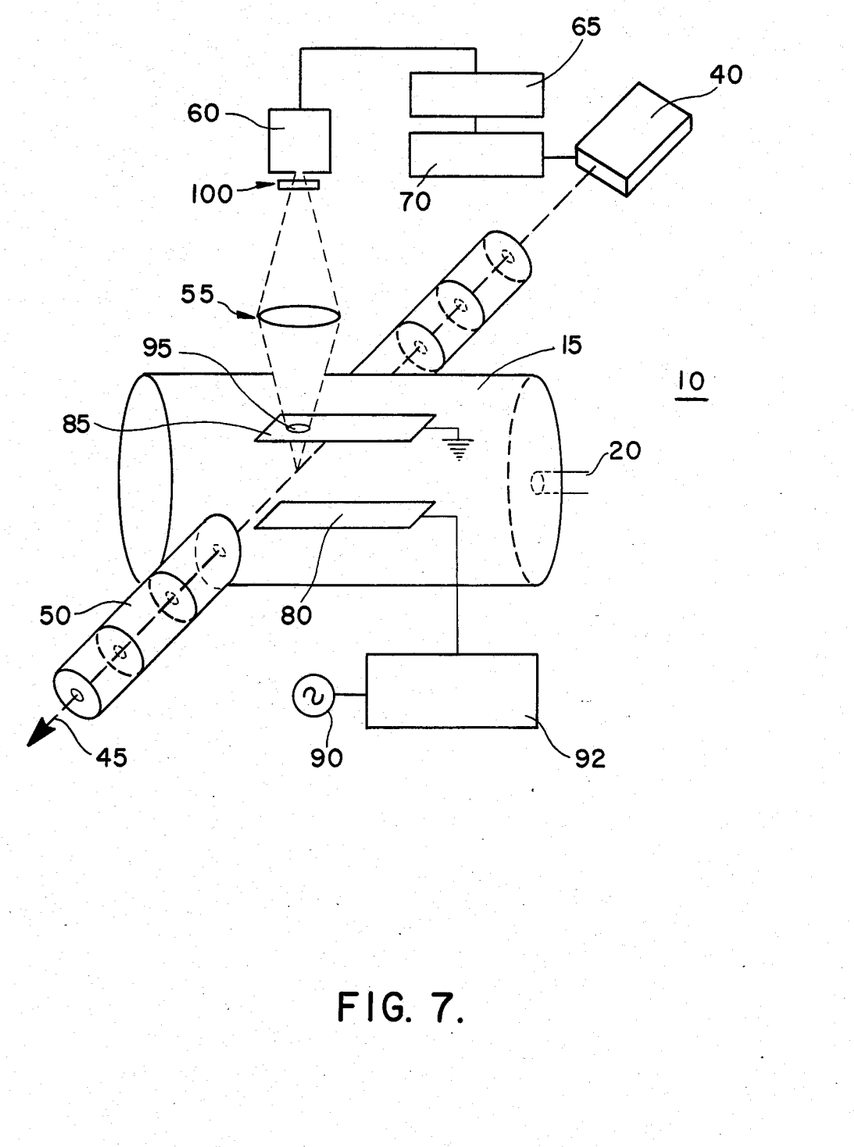
FIG. 7 is a schematic of an illustrative apparatus using the methods of the invention for probing a glow discharge reactor by laser-induced fluorescence.

The apparatus illustrated in FIG. 1 was easily modified for the laser-induced fluorescence detection of radical species in a radio frequency glow discharge. As illustrated in FIG. 7 (similar numerals represent similar parts on the apparatus described in FIG. 1), electrodes 80, 85 placed in a reactor 15 consists of two parallel 4×24 centimeter stainless steel plates, one of which is connected to a variable-frequency r.f. power supply 90 and matching network 92. The discharge is typically operated in the range of 100 KHz and at 10 W. The laser beam 40 was directed parallel to the electrodes 80, 85 and the fluorescence passes through a hole 95 of approximately 1 centimeter in diameter on the upper electrode 85. Suitable band-pass filters 100 were used to block out the discharge emission occurring outside the region of interest which was predetermined to be 400-450 nm.

Figure 8:
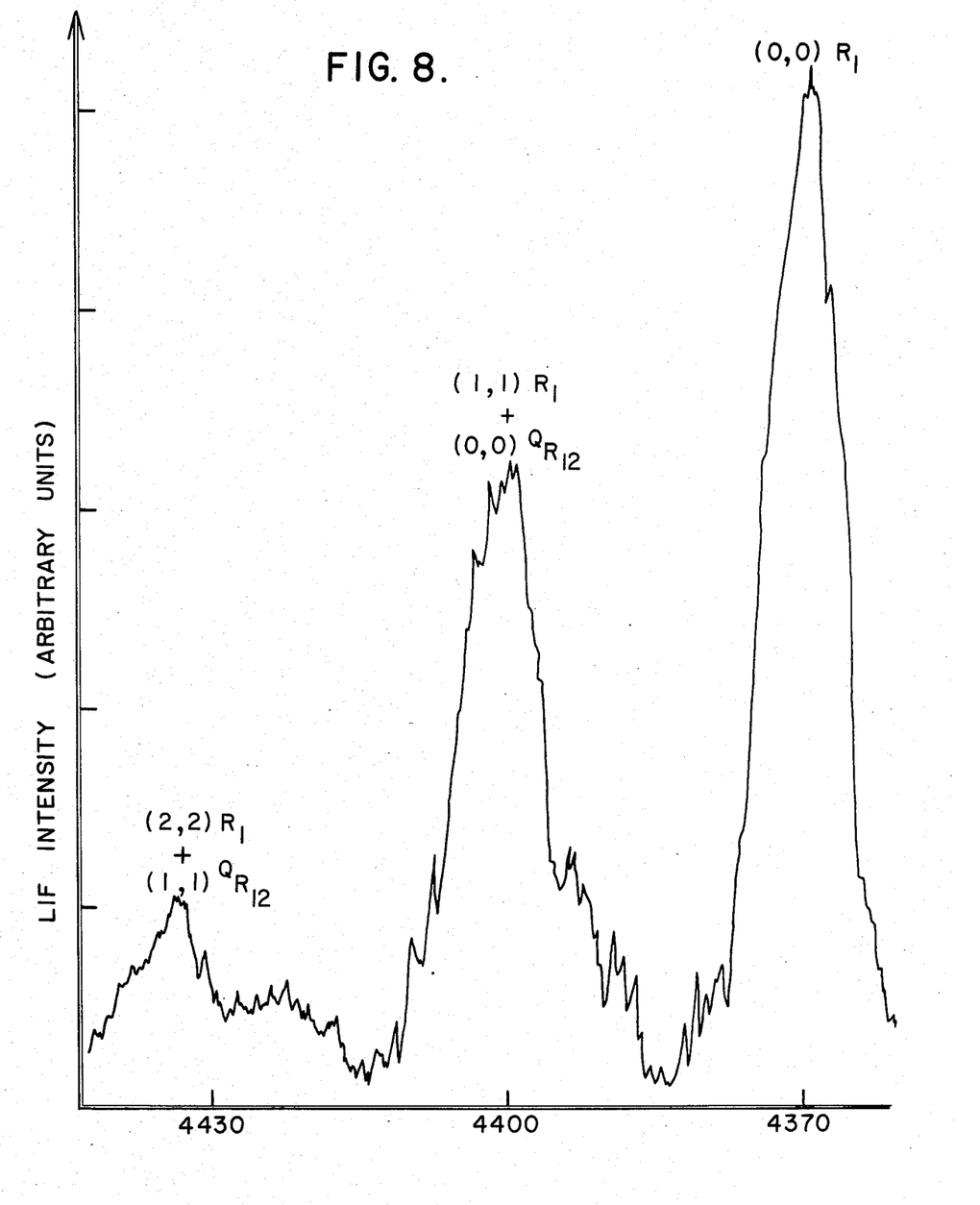
FIG. 8 is a spectrum of laser-induced fluorescence excitation obtained from the decomposition of $SiF_4$ in a glow-discharge reactor demonstrating the detection of SiF.

FIG. 8 is a spectrum of laser-induced fluorescence excitation detecting SiF in the discharge decomposition of SiF$_4$ at a pressure of 0.5 Torr. This illustrates the successful use of laser-induced fluorescence to the detection of chemical intermediates or transient species present in glow-discharge decomposition reactors. Although the laser-induced fluorescence signals in this spectra are far weaker than in the diffusion flame reaction, the SiF species shows up clearly in the excitation spectrum as assigned therein. Analysis of these laser-induced fluorescence spectra indicates a vibrational temperature of about 700–900K for the SiF product.

Figure 9:
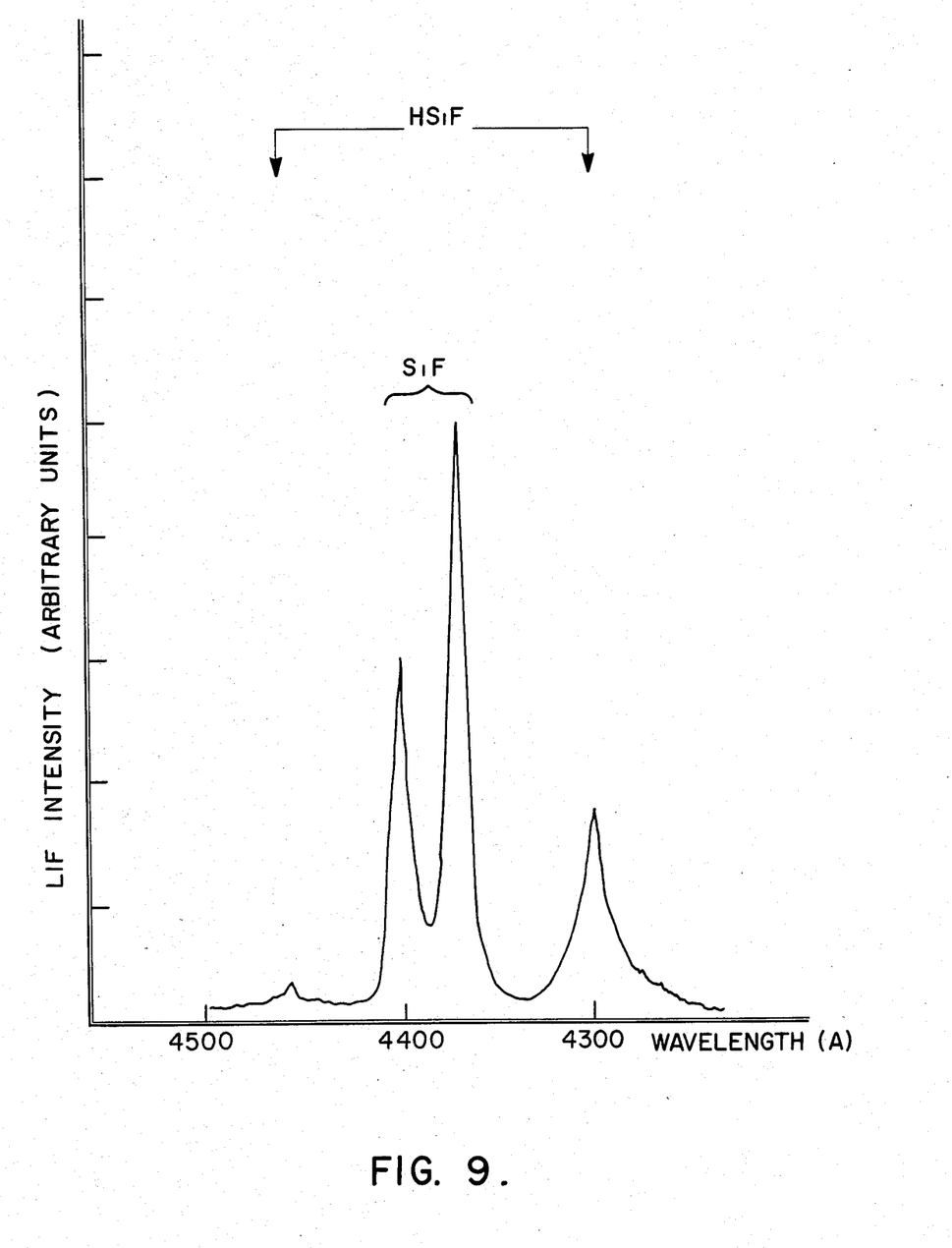
FIG. 9 is a spectrum of laser-induced fluorescence excitation obtained from the r.f. discharge of a mixture of $SiH_4$ and $SiF_4$ demonstrating the detection of SiHF and SiF.

A mixture of $SiH_4$ and $SiF_4$ was analyzed for the laser-induced fluorescence excitation obtained from the radio frequency glow discharge of the mixture. FIG. 9 presents the spectrum of the excitation obtained emphasizing the detection of the transient species SiHF and SiF produced by the plasma reaction. No laser-induced fluorescence signal was observed unless the plasma was generated.

A mixture of $SiF_4$ and hydrogen was analyzed for the laser-induced fluorescence excitation obtained from the radio frequency glow discharge of the mixture. A spectrum essentially identical to the one illustrated in FIG. 9 emphasizes the detection of SiHF and SiF.

The present invention includes methods for depositing a material on a substrate. These methods induce a deposition reaction having at least one reactant. The deposition reaction may use a diffusion flame, or preferably, a plasma such as created by a glow discharge. The deposition reaction is positioned in operative contact with a substrate so that the product of the deposition reaction is a body of material deposited on the substrate.

Preferred reactants used in a diffusion flame deposition reaction includes a mixture of fluorine or fluorine containing compounds with at least one of the following reactants: $SiH_4$, $SiH_3F$, $SiH_2F_2$, $GeH_4$, $GeH_3F$, and $GeH_2F_2$. More than one of these reactants may be combined in the mixture. Other reactants which include atoms of silicon or germanium are suitable.

Preferred reactants used in a plasma deposition reaction includes at least one of the following reactants: $SiH_4$, $SiH_3F$, $SiH_2F_2$, $SiHF_3$, $SiF_4$, $GeH_4$, $GeH_3F$, $GeH_2F_2$, $GeHF_3$, and $GeF_4$. More than one of these reactants may be combined in a mixture. These reactants also may be used singly, or in combination, with hydrogen. Other reactants which include atoms of silicon or germanium are suitable.

The method also includes detecting a species in the deposition reaction. Preferably, the species has at least one attractive or stable excited state. The formula for the species is preferably $SiH_2$, SiH, SiHF, SiF, $SiF_2$, $GeH_2$, GeH, GeHF, GeF, and $GeF_2$. Other suitable species include either silicon or germanium atoms. Not only is the mere presence of a particular species detected, but its concentration relative to the other species present may be measured. Preferably, the detecting step further includes inducing fluorescence of the species with an optical excitation source such as a laser, and measuring the relative concentration of the species.

An important feature of the invention is the control obtained by adjusting the deposition reaction in response to the concentration of a selected species present in the deposition process. Monitoring such a species which occurs in a deposition reaction allows adjustment of the deposition reaction conditions to control the species within a predetermined concentration range. These conditions include, for example, intensity of reaction perturbing laser-excitation, reactor temperature, reactor pressure, flow rates of the input reactants and reactor throughput. Adjusting these conditions in response to the relative concentration of the monitored species allows ultimate control of the quality and quantity of the material being deposited.

Another important feature of the invention is the control obtained with the deposition process by perturbing the deposition reaction so that the deposited material is modified. This method of control selectively excites an effective concentration of a species which will perturb the deposition reaction itself and modify the deposited material. Not only may the particular species to be excited be selected, but the particular stable excited state also may be selected. The species may be a precursor of the material finally deposited. Again, the invention affords ultimate control over the composition, structure, and quality i.e. uniformity, homogeneity, etc. of the deposited material. Preferably, a laser is used as the optical excitation source to excite the species to one of its stable excited states. The concentration of the species should be sufficient to have the desired effect of modifying the deposited material.

For efficient perturbation of a deposition reaction by creating a stable excited state species, it is desirable to tune the optical excitation source to a frequency at which the optical absorption is highest. Such a frequency coincides with the excitation frequency for maximum intensity of laser-induced fluorescence signals. Examples of suitable wavelengths (in nanometers) corresponding to the efficient excitation of particular species include: $SiH_2$, 579.7; $SiH_4$, 414.2; SiHF, 430.0; SiF, 436.8; $SiF_2$, 380.0; GeH, 389.8; GeF, 431.1; and $GeF_2$, 325.6.

The above described methods are particularly useful for depositing a photoconductive film on a substrate. The substrate is positioned in operative contact with a deposition reaction in a reactor. Either a diffusion flame or a plasma is suitable for inducing such a reaction. The deposition method detects a transient species having a stable excited state by inducing the fluorescence of the species with an optical excitation source, preferably a laser, and measuring the relative concentration of the species. Preferably, the deposited film is amorphous $SiH_XF_Y$, wherein either X or Y are greater than or equal to zero and less than or equal to 0.2.

An apparatus useful in performing the methods described above includes a reactor for inducing a deposition reaction in operative contact with a substrate preferably with either a diffusion flame or plasma. The reactor may include means for introducing a reactant into the reactor to induce a flow reaction. An optical excitation source such as a laser is positioned for probing the reactor. The apparatus includes means for detecting a species present in the deposition reaction, inducing the fluorescence of the species with the optical excitation source, and measuring the relative concentration of the species. An example of a suitable optical excitation source is a laser.

Another apparatus embodiment is specifically useful for depositing an improved material. As previously described a deposition reaction is induced in a reactor. A species is present in the deposition reaction which is a precursor to the material to be deposited as the product of the deposition reaction. The apparatus includes means for exciting an effective concentration of the species to a stable excited state in order to perturb the deposition reaction. The product of the perturbed deposition reaction is a modified deposited material of improved quality. Suitable means for exciting the species include an optical excitation source such as a laser.

The present invention contemplates improved photovoltaic devices which include an improved photoconductive material made by the apparatus embodiments and methods described above. Such a photoconductive material is deposited in a suitable manner such as on a substrate while in operative contact with an effective concentration of a species for modifying the deposited material. The species is a precursor to the deposited material and is induced to a stable excited state during the deposition of the material. An optical excitation source such as a laser is a suitable means for inducing the species to one of its stable excited states. The deposition reaction used to make the photoconductive material preferably uses a diffusion flame of plasma.

The present invention demonstrates the advantages of using laser-induced fluorescence to detect the concentrations of transient species in flow reactions with enhanced sensitivity and without perturbing the reaction itself. The methods described herein can analyze a deposition reaction with pinpoint spatial accuracy. The methods presented herein allow for the monitoring and controlling of a deposition process through analysis of the deposition reaction itself and detection of the mere presence of a species or its relative concentration.

Increasing the concentration of a selected species and a particular excited state by tunable laser or other source of optical excitation can be an advantageous modification technique for improving the quality of a deposited material. A relatively high power laser can be used as a perturbative means for selectively exciting a species present in the deposition reaction. Thus, the depositing process can be accurately monitored and controlled to deposit the desired material.

Modifications and variations of the present invention are possible in light of the above teachings. It is, therefore, to be understood that within the scope of the appended claims the invention may be practiced otherwise than as specifically described.

What is claimed is:

1. A method of detecting a species which is a product of a chemical flow reaction occurring in a plasma, the method comprising the steps of:
   generating a plasma to initiate a chemical flow reaction between at least two reactants producing a species having at least one electronically excited state;
   inducing the fluorescence of said species with a laser in said plasma without perturbing said flow reaction;
   measuring the fluorescence of said species in situ.

2. A method as defined in claim 1, wherein said species contains either silicon or germanium atoms.

3. A method as defined in claim 1, wherein said species is selected from the group consisting of $SiH_2$, $SiH$, $SiHF$, $SiF$, $SiF_2$, $GeH_2$, $GeH$, $GeHF$, $GeF$, and $GeF_2$.

4. A method as defined in claim 1, wherein said flow reaction includes at least one of the reactants selected from the group consisting of $SiH_4$, $SiH_3F$, $SiH_2F_2$, $SiHF_3$, $SiF_4$, $GeH_4$, $GeH_3F$, $GeH_2F_2$, $GeHF_3$, and $GeF_4$.

5. A method as defined in claim 4, wherein said flow reaction further includes hydrogen.

6. A method of detecting a species which is a product of a chemical flow reaction occurring in a diffusion flame, the method comprising the steps of:
   generating a diffusion flame to initiate a chemical flow reaction between at least two reactants producing a species having at least one electronically excited state;
   including the fluorescence of said species with a laser in a diffusion flame without perturbing said flow reaction;
   measuring the fluorescence of said species in situ.

7. A method as defined in claim 6, wherein said species contains either silicon or germanium atoms.

8. A method as defined in claim 6, wherein said species is selected from the group consisting of $SiH_2$, $SiH$, $SiHF$, $SiF$, $SiF_2$, $GeH_2$, $GeH$, $GeHF$, $GeF$, and $GeF_2$.

9. A method as defined in claim 6, wherein said flow reaction includes a mixture of fluorine or a fluorine containing compound with at least one of the following species $SiH_4$, $SiH_3F$, $SiH_2F_2$, $GeH_4$, $GeH_3F$, and $GeH_2F_2$.

10. A method of depositing a semiconductor material on a substrate comprising the steps of:
    generating a deposition reaction having a species which is a product of a chemical flow reaction using either a diffusion flame or plasma, said deposition reaction in operative contact with a substrate so that the product of said deposition reaction is a body of material deposited on said substrate;
    perturbing said deposition reaction in situ by exciting an effective concentration of said species to an electronically excited state so that the deposited semiconductor material is modified, said species being a precursor to the deposited semiconductor film; and
    depositing said material on said substrate.

11. A method as defined in claim 10, wherein said method further comprises controlling said deposition reaction of said generating step in response to the relative concentration of said species.

12. A method as defined in claim 10, wherein said excitation is laser induced.

13. A method as defined in claim 10, wherein said depositing step includes perturbing said deposition reaction by exciting an effective concentration of said species to a stable excited state so that the deposited material is modified.

14. A method of depositing a photoconductive film comprising the steps of:
    generating a chemical dissociation deposition reaction between at least two reactants using either a diffusion flame or plasma, said deposition reaction in operative contact with a substrate so that the product of said deposition reaction is a photoconductive film deposited on said substrate;
    detecting a transient species having an electronically excited state by inducing the fluorescence of said species with an optical excitation source and monitoring and correlating in situ the relative concentration of said species with the quality of said photoconductive film; and
    depositing said photoconductive film on said substrate.

15. A method as defined in claim 14, wherein said species is selected from the group consisting of $SiH_2$, $SiH$, $SiHF$, $SiF$, $SiF_2$, $GeH$, $GeH_2$, $GeHF$, $GeF$, and $GeF_2$.

16. A method as defined in claim 14, wherein said reactant includes at least one of the reactants selected from the group consisting of $SiH_4$, $SiH_3F$, $SiH_2F_2$, $SiHF_3$, $SiF_4$, $GeH_4$, $GeH_3F$, $GeH_2F_2$, $GeHF_3$, and $GeF_4$.

17. A method as defined in claim 14, wherein said reactant is a mixture of fluorine or a fluorine containing compound with at least one of the following species SiH$_4$, SiH$_3$F, SiH$_2$F$_2$, GeH$_4$, GeH$_3$F, and GeH$_2$F$_2$.

18. A method as defined in claim 14, wherein said method further comprises controlling said deposition reaction of said inducing step in response to the relative concentration of said species.

19. A method as defined in claim 14, wherein said depositing step further includes perturbing the deposition reaction by exciting an effective concentration of said species to a stable excited state so that the deposited photoconductive film is modified.

20. A method as defined in claim 14, wherein said optical excitation source is a laser.

21. The method as defined in claim 10 wherein said species is selected from the group consisting of SiH$_2$, SiH$_4$, SiHF, SiF, SiF$_2$, GeH, GeF and GeF$_2$ and said frequency for highest optical absorption is, respectively: SiH$_2$, 579.7 nanometers; SiH$_4$, 414.2 nanometers; SiHF, 430 nanometers; SiF, 436.8 nanometers; SiF$_2$, 380 nanometers; GeH, 389.8 nanometers; GeF, 431.1 nanometers; and GeF$_2$, 325.6 nanometers.

22. The method as defined in claim 12 wherein the frequency of said laser excitation corresponds to the frequency where the optical absorption for said species is the highest.

23. The method as defined in claim 20 wherein the frequency of said laser excitation corresponds to the frequency where the optical absorption for said species is the highest.

24. The method as defined in claim 23, wherein said species is selected from the group consisting of SiH$_2$, SiH$_4$, SiHF, SiF, SiF$_2$, GeH, GeF, and GeF$_2$ and said frequency for highest optical absorption is, respectively, SiH$_2$, 579.7 nanometers; SiH$_4$, 414.1 nanometers; SiHF, 430 nanometers; SiF, 436.8 nanometers; SiF$_2$, 380 nanometers, GeH, 389.8 nanometers; GeF, 431.1 nanometers; and GeF$_2$, 325.6 nanometers.

* * * * *